(12) United States Patent
Nicolette

(10) Patent No.: US 6,960,183 B2
(45) Date of Patent: Nov. 1, 2005

(54) VETERINARY PILL AND CAPSULE DELIVERY DEVICE

(76) Inventor: Jon R. Nicolette, 2106 Hampshire Dr., Fallston, MD (US) 21047-1424

( * ) Notice: Subject to any disclaimer, the term of this patent is extended or adjusted under 35 U.S.C. 154(b) by 47 days.

(21) Appl. No.: 10/726,975

(22) Filed: Dec. 2, 2003

(65) Prior Publication Data

US 2004/0111053 A1 Jun. 10, 2004

Related U.S. Application Data

(60) Provisional application No. 60/430,194, filed on Dec. 2, 2002.

(51) Int. Cl.[7] .................. A61M 31/00; A61M 13/00; A61M 5/14; A61M 37/00; A61B 1/00
(52) U.S. Cl. .................. 604/57; 600/106; 604/58; 604/59; 604/60; 604/140; 604/82
(58) Field of Search .................. 604/51–68, 140–145, 604/218, 222, 191, 416, 82; 600/106, 101, 104; 606/236; 119/51.01

(56) References Cited

U.S. PATENT DOCUMENTS 5,643,206 A * 7/1997 Fischer .................. 604/82
5,681,279 A * 10/1997 Roper et al. .................. 604/57
6,139,530 A * 10/2000 Hiejima et al. .................. 604/140

* cited by examiner

*Primary Examiner*—Nicholas D. Lucchesi
*Assistant Examiner*—Roz Maiorino
(74) *Attorney, Agent, or Firm*—Law Offices of Royal W. Craig

(57) ABSTRACT

A veterinary pill/capsule delivery device comprised of a dispensing head for holding a pill or capsule, the dispensing head being attached to the end of a syringe component for ejecting the pill or capsule out from the dispensing head into the animal's mouth while at the same time injecting a quantity of water into the mouth. The syringe component includes a push-rod that protrudes into dispensing head for ejecting the pill/capsule therefrom, plus water release holes near the dispensing head for simultaneously jetting water out of the syringe component into the animal's mouth, thereby compelling the animal to swallow the pill.

14 Claims, 4 Drawing Sheets

VETERINARY PILL AND CAPSULE DELIVERY DEVICE

CROSS-REFERENCE TO RELATED APPLICATIONS

The present application derives priority from U.S. Provisional Patent Application No. 60/430,194 for "VETERINARY PILL AND CAPSULE DELIVERY DEVICE", filed Dec. 2, 2002.

BACKGROUND OF THE INVENTION

1. Field of the Invention

The present invention relates to veterinary tools and, more particularly, to a veterinary pill and capsule delivery device for simplifying the dispensing of pills and capsules to animals.

2. Description of the Background

Most of the time medication is prescribed for pets in the form of either a pill or a capsule. As every pet owner knows, it is difficult to get a pill into the back of an animal's mouth, particularly by one person; yet it is almost impossible to get the pet to swallow the pill or capsule even if one can get it into the back of the animal's mouth. Animals are capable of holding the medication in their esophagus for several minutes and then spitting it out.

There is a commercially-available device called a Piller that helps to deposit the pill into the mouth, but does not facilitate swallowing. Without a method to induce swallowing, the pet attempts to push out the pill or holds it in the mouth or throat, only to spit it out later.

Similarly, U.S. Pat. No. 5,584,805 to Sutton issued Dec. 17, 1996 shows an animal pill-dispenser gun designed for pushing a pill into the throat of cattle and other animals to administer medicine with a sleeve and a core extending through the interior of the outer member and up into the barrel of the gun.

Unfortunately, none of the foregoing or any other known veterinary devices help to ensure that the pill that has been inserted is then swallowed.

Thus, there is a significant commercial need for a pill-dispenser that not only deposits a pill in the animal's mouth, but also induces them to swallow.

SUMMARY OF THE INVENTION

Accordingly, it is an object of the present invention to provide a pill dispensing device that not only helps to put the pill or capsule into the back of the animal's mouth, but also simultaneously dispenses a small amount of water to stimulate peristalsis and lubricate the esophagus which results in proper swallowing of the medication.

It is another object to provide a pill dispensing device that is inexpensive and easy to manufacture.

It is yet another object to provide a pill dispensing device that is easy to use to dispense medication to an animal by a single person.

In accordance with the foregoing objects, the present device comprises a dispensing head for holding the pill or capsule, and a syringe component for ejecting the pill or capsule out from the dispensing head into the animal's mouth while at the same time injecting a quantity of water into the mouth.

The dispensing head is a split rubber tip for holding the pill by compression fit at the end of the syringe component. The syringe component comprises a modified double-barrel hypodermic syringe with no needle. The syringe has a standard barrel and thumb-operable plunger for ejecting water. However, the standard barrel leads to a smaller-diameter tube in fluid communication with the barrel, and a piston is slidably mounted in the tube. A push-rod is mounted forwardly on the piston and is contained in the tube. Upon thumb-operation of the plunger, water is urged into the tube, and this urges the piston and push-rod forward as well. The push-rod ejects the pill/capsule from the dispensing head into the animal's mouth. At the same time, the piston moves past water release holes in the tube (near the dispensing head) and the water is jetted out of the water release holes into the animal's mouth, thereby compelling the animal to swallow the pill.

BRIEF DESCRIPTION OF THE DRAWINGS

Other objects, features, and advantages of the present invention will become more apparent from the following detailed description of the preferred embodiment and certain modifications thereof when taken together with the accompanying drawings in which.

DETAILED DESCRIPTION OF THE PREFERRED EMBODIMENTS

The present invention is a pill dispensing device that not only helps to eject and insert a pill or capsule into the back of an animal's mouth, but also simultaneously dispenses a small amount of water to stimulate peristalsis and lubricate the esophagus. The foregoing results in proper and immediate swallowing of the medication. The invention will be described with reference to one particular embodiment that can be economically manufactured.

Figure 1:
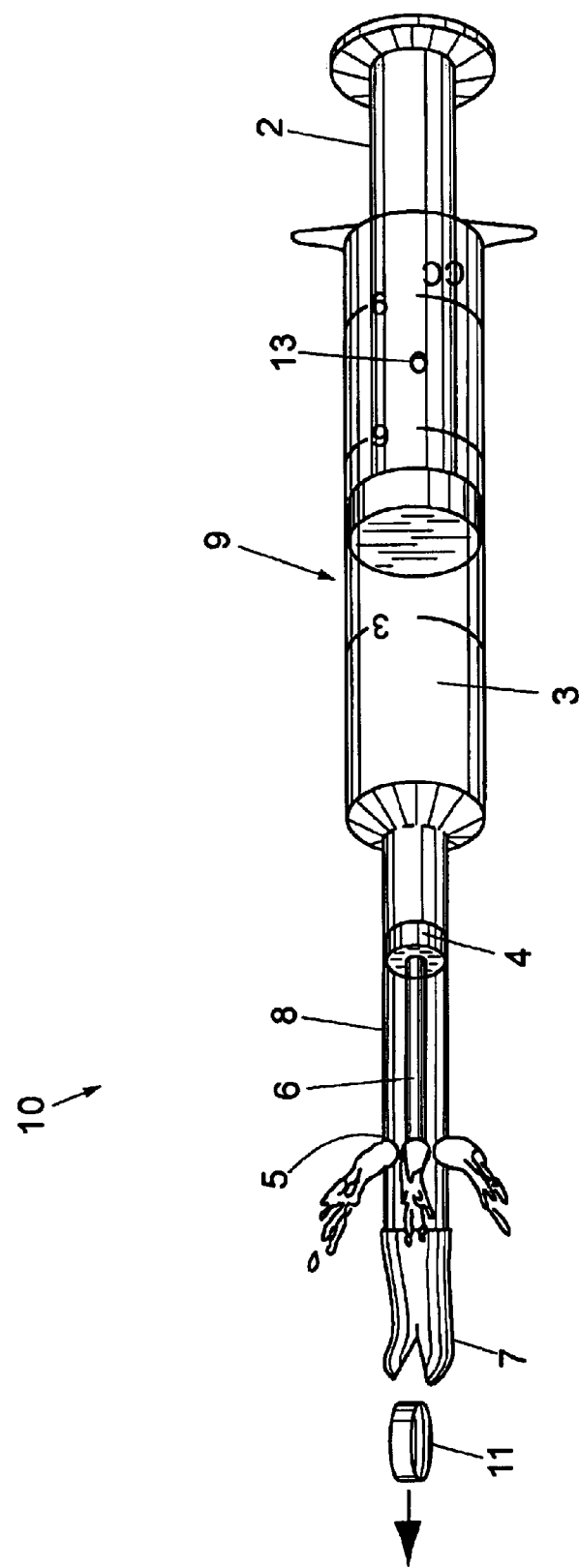
FIG. 1 is a side perspective view of the veterinary pill and capsule delivery device 10 jetting water while depositing a pill 11 according to the present invention.

As shown in FIG. 1, the pill and capsule delivery device 10 generally comprises a dispensing head 7 for holding a pill or capsule 11, and a syringe component 9 for ejecting the pill or capsule out from the dispensing 7 head into the animal's mouth while at the same time injecting a quantity of water into the mouth.

In the illustrated embodiment, the dispensing head 7 is a split rubber tip for holding the pill 11 by compression fit at the end of the syringe component 9. The syringe component 9 further comprises modified double-barrel hypodermic syringe with no needle. The syringe component 9 has a standard barrel 3 and thumb-operable plunger 2 for ejecting water. However, the standard barrel 3 leads to a smaller-diameter tube 8 which is in fluid communication with the barrel 3, and a piston 4 is slidably mounted in the tube. A push-rod 6 is mounted forwardly on the piston 4 and is contained in the tube 8.

In the illustrated embodiment at least one small air pressure release hole 13 penetrates the barrel 3 at a position along its length. One or more air pressure release holes 13 may be molded or otherwise formed therein at a lengthwise location that depends on the desired amount of water to be ejected (larger animals will require more water than smaller animals). The air pressure release hole(s) 13 allow air to escape from the main barrel 3 when first pushing plunger 3, thereby bleeding air and allowing the user to dispense the desired barrel full of a proper amount of water without air.

Upon thumb-operation of the plunger 2, water is urged into the tube 8, and this urges the piston 4 and push-rod 6 forward as well. The push-rod 6 ejects the pill/capsule 11 from the dispensing head 7 into the animal's mouth. At the same time, the piston 4 moves past water release holes 5 in the tube 8 (near the dispensing head 7) and the water is jetted out of the water release holes 5 into the animal's mouth, thereby compelling the animal to swallow the pill 11.

Figure 2:
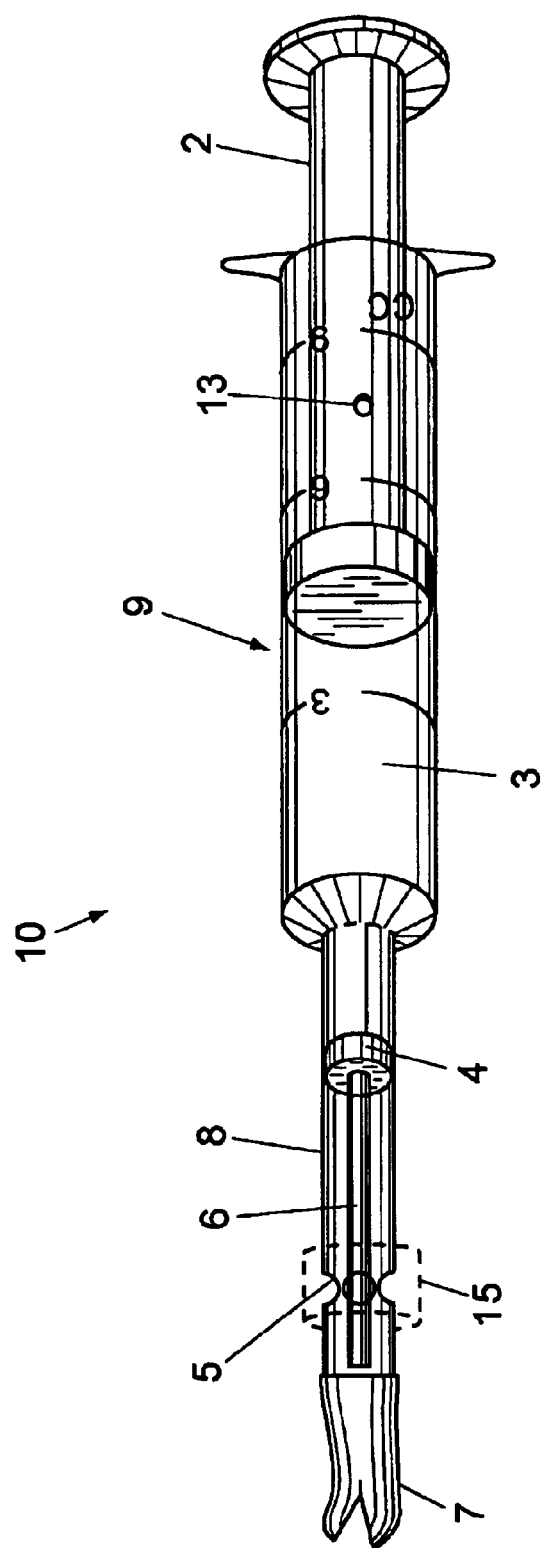
FIG. 2 is a side perspective view of an idle veterinary pill and capsule delivery device 10 as in FIG. 1.
Figure 3:
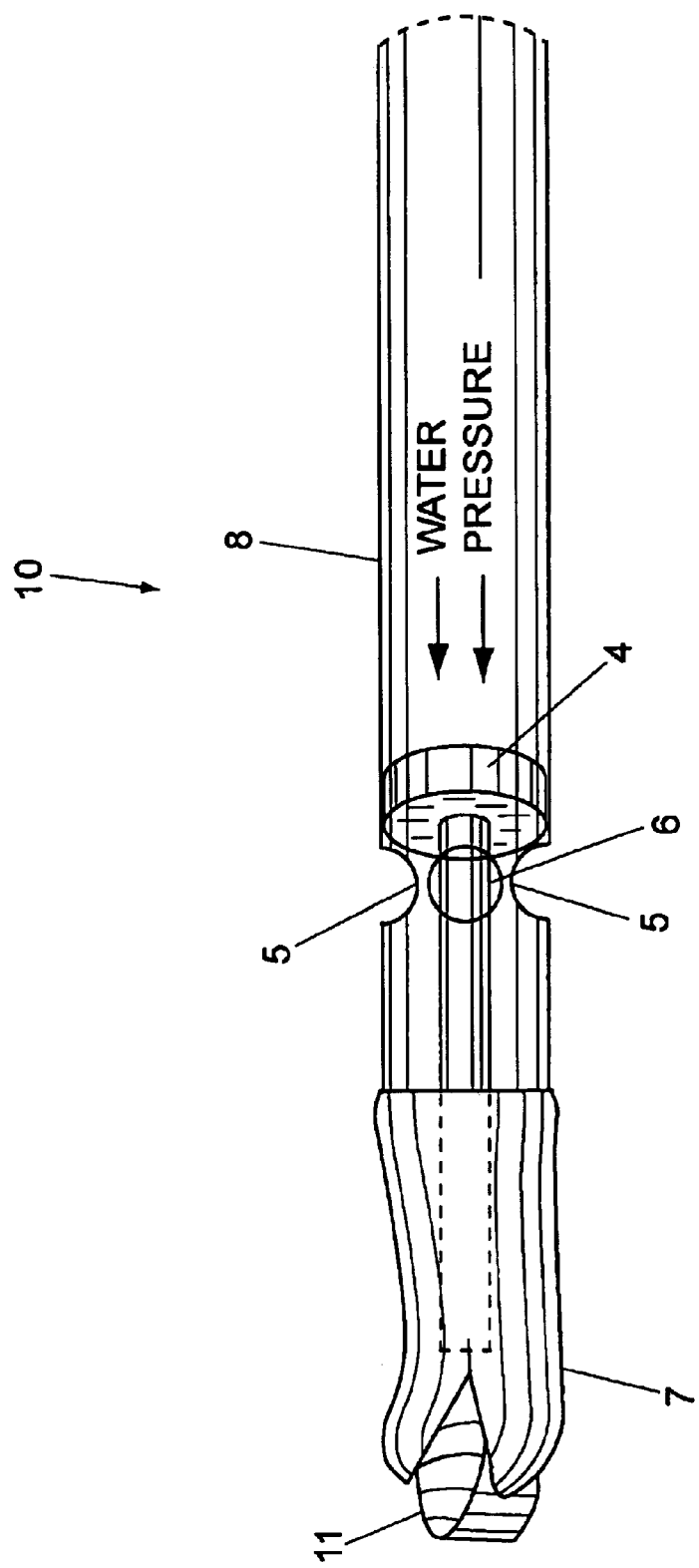
FIG. 3 is an enlarged perspective view of the dispensing head 7 of the veterinary pill and capsule delivery device 10, before pushing plunger.
Figure 4:
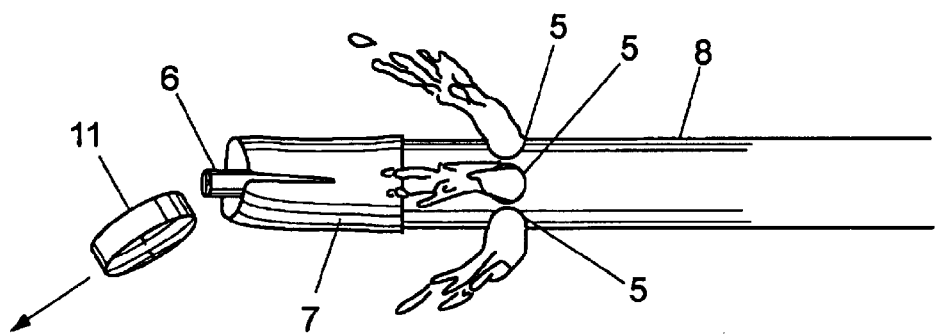
FIG. 4 is an enlarged perspective view of the dispensing head 7 of the veterinary pill and capsule delivery device 10, after pushing plunger.

FIG. 2 is a side perspective view of an idle veterinary pill and capsule delivery device 10 as in FIG. 1, and FIG. 3 is an enlarged perspective view of the dispensing head 7, before pushing plunger 2.

As seen collectively in FIGS. 1–3, the water release holes 5 are located near the tip of the tube 8 just behind the dispensing head 7. The dispensing head 7 is an annular piece of molded rubber or other elastic material, formed with an open end and a normally-closed end, the latter being defined by a mouth formed by a lateral cut into the closed-end molded rubber component. The mouth of dispensing head 7 is therein formed by a pair of resilient rubber jaws for releasably gripping pills or capsules 11 in a variety of sizes. The open end of the dispensing head 7 is dimensioned for a compression fit onto the end of the tube 8.

Water release holes 5 are a series of radially-spaced apertures molded or cut into the distal end of the tube 8 in advance of the fitted dispensing head 7. The water release holes 5 may be varied in size, shape and/or angular orientation in accordance with the desired amount, spray pattern, and spray angle of water to be jetted outward, which in turn depends on the relative size and mouth of the type of animal the device 10 will be used for. If desired (as shown in broken lines in FIG. 2), a deflector 15 may be molded or integrally-formed about the water release holes 5 to direct the water into the back of the mouth and to prevent splashing. The internal push-rod 6 with integral distal piston 4 is adapted for slidable insertion inside the tube 8, piston 4 first, in front of the plunger 2.

In one exemplary manufacturing method for assembling the device 10 for use, the syringe plunger 2 is inserted into the open end of the main barrel 3, and the internal push-rod 6 with integral distal piston 4 is inserted into the tube 8, piston 4 first, in front of the plunger 2. The dispensing head 7 is then attached to the distal end of the tube 8.

In operation of the device 10, the syringe plunger 2 is removed and the main barrel 3 is filled with water. A pill or capsule 11 is then inserted into the jaws of the dispensing head 7. Gripping the device 10 with thumb and forefingers, the pill 11 (held in the jaws of the dispensing head 7) is inserted into the mouth of the animal, preferably oriented into the throat, and the syringe component 9 is operated by thumb just as a conventional syringe. The plunger 2 is urged forwardly, and initially the air pressure release hole(s) 13 will allow air to bleed from the main barrel 3, thereby ensuring that a proper amount of water is dispensed without air. When the plunger 3 advances past the air pressure release hole(s) 13, water pressure begins to build in the space between the plunger 2 and piston 4. The water pressure advances the piston 4 and push rod 6 through the tube 8 until the push-rod protrudes outward through the jaws of the dispensing head 7, thereby ejecting the pill 11 held therein into the animal's mouth. At the same time, the piston 4 moves forward of the water release holes 5, and the dose of water is jetted outward from the water release holes 5 down into the animal's throat. This ejected water not only helps to sweep the pill or capsule 11 into the back of the animal's mouth, but also stimulates peristalsis, lubricates the esophagus, and compels the animal to swallow. The foregoing results in proper injestion of the medication.

The above-described device 10 is easy to use and highly effective for dispensing medication to an animal by a single person, and is also inexpensive and easy to manufacture as it entails a simple modification to existing syringes.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. For example, the plunger 2 may be attached rearwardly to the piston 4 by a rod (the full push-rod 6, piston 4 and plunger 2 assembly being integrally formed). It is to be understood, therefore, that the invention may be practiced otherwise than as specifically set forth in the appended claims.

I claim:

1. A pill or capsule delivery device for ejecting a pill or capsule into an animal's mouth while at the same time injecting a quantity of water into the mouth, comprising:

a dispensing head for releasably holding a pill or capsule; and a syringe component including a main barrel for containing a dose of water, a thumb-operable plunger insertable to one end of said main barrel for urging said water forward, a tube in fluid communication with the other end of said main barrel and upon which said dispensing head is distally mounted, said tube being defined by at least one water release hole proximate said dispensing head, a piston slidably mounted in the tube for traversing said at least one water release hole to thereby eject said dose of water, said piston including a push-rod extending toward said dispensing head and movable by water pressure against said piston to protrude into said dispensing head;

whereupon thumb-operation of the plunger, said water urges the piston and push-rod forward such that said push-rod ejects the pill/capsule from the dispensing head into the animal's mouth, and when the piston clears said at least one water release hole in the tube said water is jetted out of the water release holes into the animal's mouth, thereby compelling the animal to swallow the pill/capsule.

2. The pill and capsule delivery device according to claim 1 wherein said dispensing head is a split rubber tip attached to the distal end of the tube.

3. The pill and capsule delivery device according to claim 2 wherein said split rubber tip comprises a pair of resilient rubber jaws which releasably hold said pill or capsule.

4. The pill and capsule delivery device according to claim 1 wherein said tube comprises a plurality of water release holes radially-spaced about a distal end of the tube proximate said dispensing head.

5. The pill and capsule delivery device according to claim 1 wherein said main barrel is filled with water by removal of the plunger therefrom.

6. The pill and capsule delivery device according to claim 1 wherein at least one air pressure release hole is formed through said main barrel along its length to allow air to escape from the main barrel before dispensing water.

7. The pill and capsule delivery device according to claim 1, further comprising a deflector partially enclosing the water release holes to direct the water into the back of the mouth and to prevent splashing.

8. A pill or capsule delivery device for ejecting a pill or capsule into an animal's mouth while at the same time injecting a quantity of water into the mouth, comprising:

a dispensing head for releasably holding a pill or capsule; and a syringe component including a main barrel for containing a dose of water, a thumb-operable plunger insertable into one end of said main barrel for ejecting said water, a tube in fluid communication with the other end of said main barrel and defined by at least one water release hole, and a push-rod engaged and by said plunger and movable therewith to protrude into said dispensing head;

a syringe component including a main barrel for containing a dose of water, a thumb-operable plunger insertable into one end of said main barrel for urging said water forward, a tube in fluid communication with the other end of said main barrel and upon which said dispensing head is distally mounted, said tube being defined by at least one water release hole, a push-rod engaged at one end by said plunger and carrying a piston along its length, said push rod extending toward said dispensing head and movable with said plunger to protrude into said dispensing head and eject the pill while said piston traverses said at least one water release hole to thereby eject said dose of water; whereupon thumb-operation of the plunger, said plunger urges the push-rod forward such that said push-rod ejects the pill/capsule from the dispensing head into the animal's mouth, and water is simultaneously jetted out of the water release holes into the animal's mouth, thereby compelling the animal to swallow the pill/capsule.

9. The pill and capsule delivery device according to claim 8 wherein said dispensing head is a split rubber tip attached to the distal end of the tube.

10. The pill and capsule delivery device according to claim 9 wherein said split rubber tip comprises a pair of resilient rubber jaws which releasably hold said pill or capsule.

11. The pill and capsule delivery device according to claim 8 wherein said tube comprises a plurality of water release holes radially-spaced about a distal end of the tube proximate said dispensing head.

12. The pill and capsule delivery device according to claim 8 wherein said main barrel is filled with water by removal of the plunger therefrom.

13. The pill and capsule delivery device according to claim 8 wherein at least one air pressure release hole is formed through said main barrel along its length to allow air to escape from the main barrel before dispensing water.

14. The pill and capsule delivery device according to claim 8, further comprising a deflector partially enclosing the water release holes to direct the water into the back of the mouth and to prevent splashing.

* * * * *